US009012188B2

(12) United States Patent
Van Heiningen et al.

(10) Patent No.: US 9,012,188 B2
(45) Date of Patent: Apr. 21, 2015

(54) CONDITIONING OF SO2-ETHANOL-WATER SPENT LIQUOR FOR FERMENTATION BY CLOSTRIDIA

(75) Inventors: Adriaan Van Heiningen, Orono, ME (US); Evangelos Sklavounos, Helsinki (FI)

(73) Assignee: API Intellectual Property Holdings, LLC, Atlanta, GA (US)

( * ) Notice: Subject to any disclaimer, the term of this patent is extended or adjusted under 35 U.S.C. 154(b) by 101 days.

(21) Appl. No.: 14/005,382

(22) PCT Filed: Mar. 16, 2012

(86) PCT No.: PCT/FI2012/050249
§ 371 (c)(1),
(2), (4) Date: Sep. 16, 2013

(87) PCT Pub. No.: WO2012/123644
PCT Pub. Date: Sep. 20, 2012

(65) Prior Publication Data
US 2014/0004582 A1    Jan. 2, 2014

(51) Int. Cl.
| | | |
|---|---|---|
| *C12P 7/12* | (2006.01) | |
| *C12P 7/04* | (2006.01) | |
| *C12P 7/28* | (2006.01) | |
| *C12P 7/16* | (2006.01) | |
| *D21C 5/00* | (2006.01) | |
| *C12P 7/10* | (2006.01) | |
| *D21C 3/06* | (2006.01) | |
| *D21C 3/20* | (2006.01) | |
| *D21C 11/00* | (2006.01) | |
| *D21C 11/02* | (2006.01) | |

(52) U.S. Cl.
CPC ... *D21C 5/00* (2013.01); *C12P 7/04* (2013.01); *C12P 7/10* (2013.01); *C12P 7/12* (2013.01); *C12P 7/16* (2013.01); *C12P 7/28* (2013.01); *D21C 3/06* (2013.01); *D21C 3/20* (2013.01); *D21C 11/0007* (2013.01); *D21C 11/02* (2013.01); *Y02E 50/16* (2013.01); *C12P 2201/00* (2013.01); *C12P 2203/00* (2013.01); *Y02E 50/10* (2013.01)

(58) Field of Classification Search
None
See application file for complete search history.

(56) References Cited

U.S. PATENT DOCUMENTS

| | | | | |
|---|---|---|---|---|
| 4,019,995 A | * | 4/1977 | Briggs et al. | 252/62.53 |
| 8,030,039 B1 | * | 10/2011 | Retsina et al. | 435/161 |
| 2007/0254348 A1 | * | 11/2007 | Retsina et al. | 435/161 |
| 2009/0236060 A1 | * | 9/2009 | Retsina et al. | 162/64 |

OTHER PUBLICATIONS

Iakovlev et al., Paper technical potential of spruce SO2-Ethanol-Water (SEW) pulp compared to kraft pulp, Nordic Pulp and Paper Research Journal, (2010), vol. 25, No. 4.*
Junelles et al., Iron Effect on Acetone-Butanol Fermentation, Current microbiology, vol. 17 (1988), pp. 299-303.*

* cited by examiner

*Primary Examiner* — Karen Cochrane Carlson
*Assistant Examiner* — Jennifer M. H. Tichy
(74) *Attorney, Agent, or Firm* — Ryan P. O'Connor

(57) ABSTRACT

The present invention relates to producing chemicals and biofuels from wood material, e.g. mixed forest biomass. Specifically, the invention concerns a process for conditioning spent liquor produced by SO$_2$-ethanol-water (SEW) fractionation of wood chips for fermentation to butanol, ethanol and acetone/isopropanol (so called ABE process) by Clostridia bacteria.

20 Claims, 3 Drawing Sheets

CONDITIONING OF SO2-ETHANOL-WATER SPENT LIQUOR FOR FERMENTATION BY CLOSTRIDIA

FIELD OF THE INVENTION

The present invention relates to producing chemicals and biofuels from wood material. Specifically, the invention concerns a process for conditioning spent liquor produced by $SO_2$-ethanol-water (SEW) fractionation of wood chips for fermentation to butanol, ethanol and acetone/isopropanol (so called ABE process) by Clostridia bacteria.

BACKGROUND OF THE INVENTION

In the $SO_2$-ethanol-water (SEW) pulping process, lignocellulosic feed stocks may be fractionated into their main components (cellulose, hemicelluloses and lignin) using a 55% (v/v) ethanol-water solution in which $SO_2$ is dissolved without any base (Na, Mg, Ca, etc.) present. The presence of $SO_2$ leads to dissolution and hydrolysis of hemicelluloses in high yield, while the lignin becomes soluble through sulfonation. The presence of ethanol leads to rapid penetration of the biomass, thereby eliminating the long heat-up time required in the acid sulphite process. Lignin is recovered by precipitation after ethanol evaporation. The absence of a base allows recovery of unreacted $SO_2$ by evaporation and steam stripping, while the low boiling point and low specific heat of ethanol (as compared to water) leads to energy efficient recovery of the pulping liquid by evaporation (Rakkolainen et al., 2009). Previous research in our laboratory has established that the $SO_2$-ethanol-water (SEW) fractionation method is capable of pulping both softwoods and hardwoods efficiently at moderate conditions (Iakovlev et al. 2011, Rakkolainen et al. 2010). The SEW pulping chemistry is employed by American Process Inc. in a patent pending biorefinery process termed AVAP™ to produce cellulosic fibers, chemicals and biofuels (Retsina and Pylkkänen, 2007). American Process Inc. also has various patent applications and patents for the SEW pulping chemistry, e.g. WO 2007/146245, WO 2010/151536, WO 2011/044378 and U.S. Pat. No. 8,030,039, disclosing variations of the process. The goal of the process is to treat lignocellulosic materials for producing alcohol and other bioproducts.

Acetone, butanol, and ethanol (ABE) may be obtained by fermentation of sugars using Clostridia bacteria (Dürre, 2008). In order to utilize the dissolved hemicellulose sugars in SEW spent liquor further processing and conditioning of the solution is required to allow fermentation by microorganisms. For example, the pH of the SEW spent liquor is very low (about 1.0) and adjustment to a neutral level is necessary to avoid harming the bacteria. Furthermore, fermentation inhibitors such as $SO_2$, ethanol, lignin, formic acid and furanic compounds, must be totally removed (Sklavounos and van Heiningen, 2010). It was shown that $SO_2$ is inhibitory to Clostridia bacteria at concentrations as low as 10-50 ppm, while formic acid and furfural are not tolerable at levels above 0.5 and 1.0 g $L^{-1}$, respectively (inhibition tests performed by Teräsvuori et al., 2010). In addition to fermentability of the final liquor, an efficient recovery of the cooking chemicals, i.e. $SO_2$ and ethanol, is required for the viability of the process. So far, it has not been possible to remove the above-mentioned inhibitors to that extent. Therefore, a constant need exists for an improved method for obtaining suitable liquor for ABE fermentation.

SUMMARY OF THE INVENTION

The present invention describes a conditioning process of the spent liquor produced by SEW fractionation of wood material. The conditioned liquor is suitable for fermentation by Clostridia bacteria, since the conditioning process reduces the final dissolved $SO_2$ concentration in the aqueous sugar stream to 10 ppm or lower, and also removes potential inhibitors from the solution. Butanol, ethanol, acetone and isopropanol are produced in significant amounts in the fermentation process. The conditioning process comprises the steps of exposing wood material to $SO_2$-ethanol-water (SEW) cooking, squeezing the pulp and recovering the spent liquor, washing the pulp to recover sugars from it and combining the washings to the spent liquor, evaporating the combined spent liquor to obtain evaporated liquor, steam stripping the evaporated liquor, liming the steam stripped liquor, and exposing the limed liquor to catalytic oxidation. Thereby, conditioned liquor suitable for fermentation with Clostridia bacteria is obtained.

DETAILED DESCRIPTION OF THE INVENTION

Figure 1:
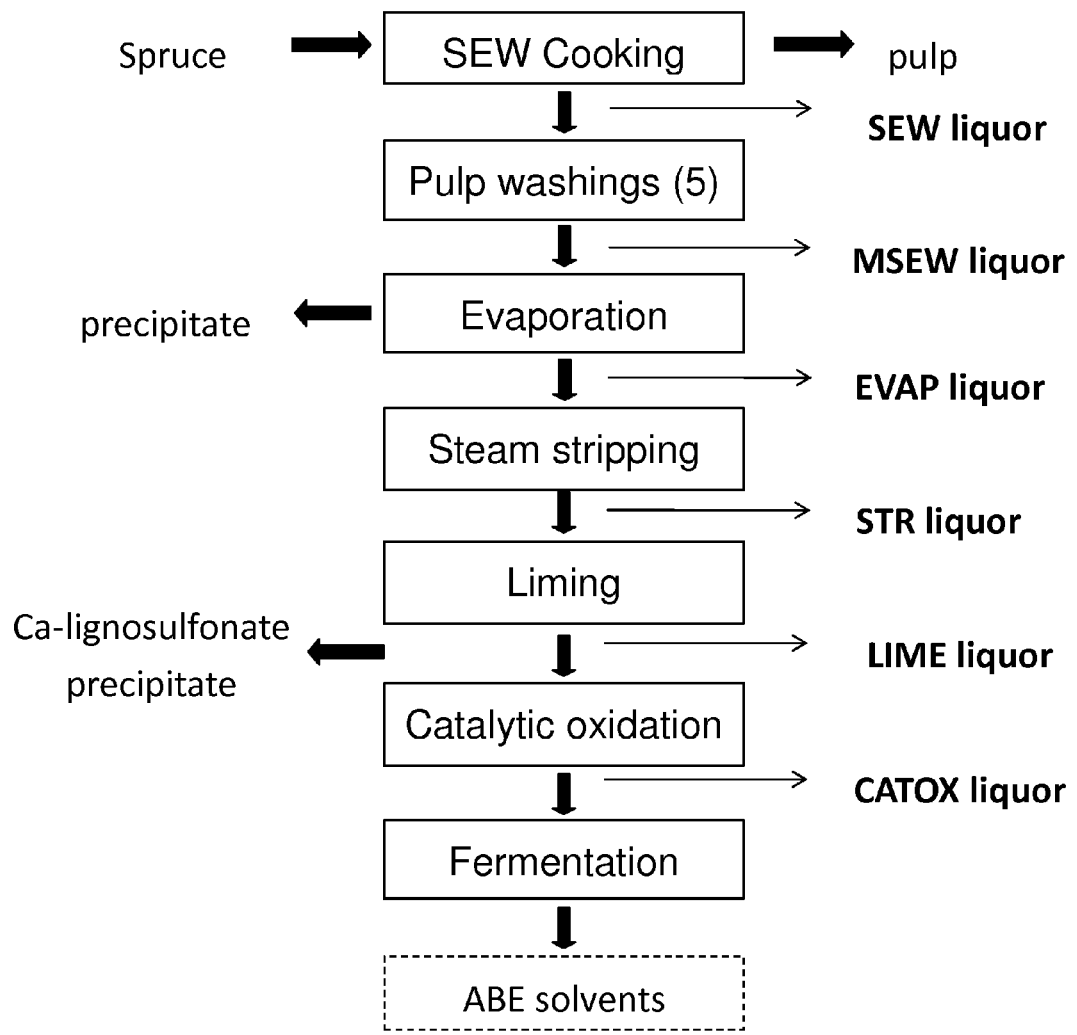
FIG. 1 Flow chart showing the conditioning process of the invention
Figure 2:
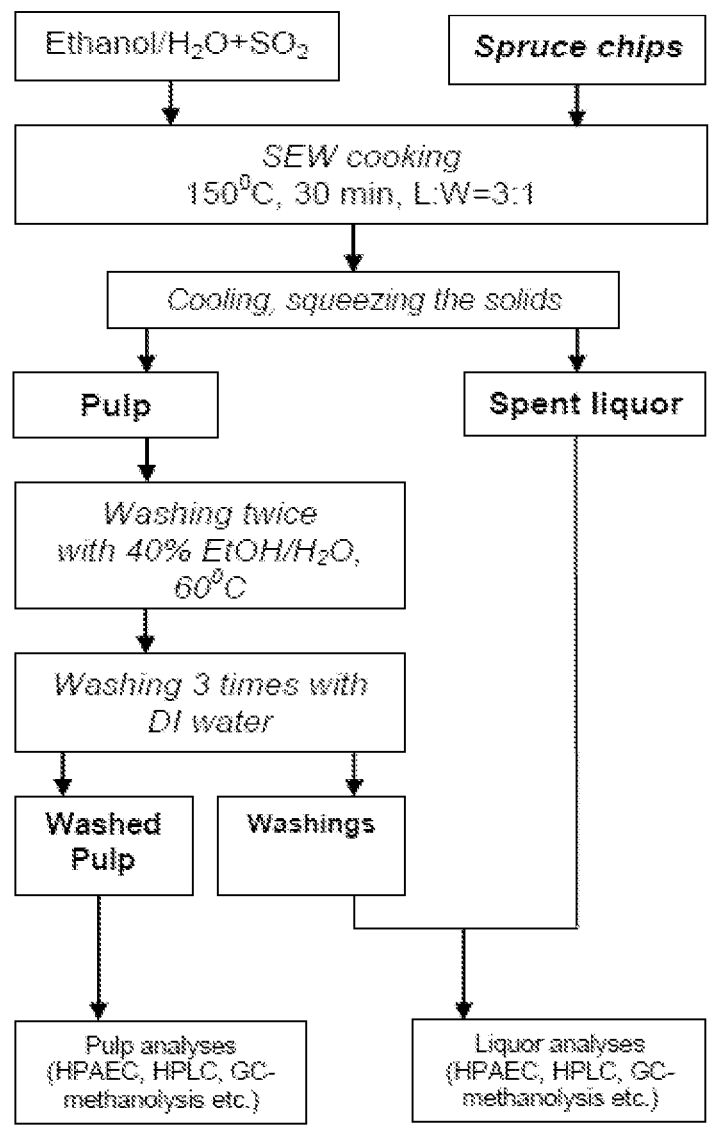
FIG. 2 Flow chart showing the details of the pulp washing step of the process of the invention FIG. 3 Graph showing the effect of pH on sulfur dioxide species

The present invention describes the $SO_2$-ethanol-water (SEW) fractionation of lignocellulosics followed by a series of process steps which "condition" the SEW spent liquor so that the dissolved lignin is recovered by precipitation and the dissolved hemicellulose wood sugars are hydrolysed to monosugars. The final liquid contains minimal amounts of inhibitors for fermentation of the monosugars to butanol, ethanol, isopropanol and acetone.

SEW fractionation is a method to fractionate lignocellulosics into its main components (cellulose, hemicellulose and lignin). The fractionation is carried out at moderate conditions by utilizing a 55% (v/v) ethanol-water solution in which high purity $SO_2$ is dissolved without any base (Na, Mg, Ca, etc.). This method offers significant advantages over other conventional pulping methods; the presence of high purity ethanol in the ethanol-water solution leads to rapid impregnation of the chips, thereby eliminating a long heat-up time which is required in the acid sulfite process. Furthermore, the presence of high purity $SO_2$ leads to maximal dissolution of hemicelluloses in high yield, and the relatively mild conditions during fractionation minimizes the formation of inhibitory compounds such as furfural and formic acid. Finally, the absence of a base eliminates the problems of tedious and costly base recovery as in the sulphate or sulfite process, while also the absence of bisulfite prevents oxidation of sugars to aldonic acids as occurs during acid sulphite pulping. However, ethanol and $SO_2$ must be recovered in high yields, both to obtain an economic process and to minimize their presence in the "conditioned" liquor since they are potential inhibitors for fermentation. Also it is advantageous to recover the chemically uncondensed lignosulfonates originating from most of the lignin in the lignocellulosics from the SEW liquor since they represent a valuable product.

The present invention successfully addresses the efficiency of SEW fractionation, and the conditioning and recovery issues of the SEW spent liquor as described in the present specification. Consequently, by using a high dissolved $SO_2$ concentration of about 12% (w/w) during SEW fractionation at 150° C. and low liquor-to-wood ratio of 3 L/kg oven dry wood or biomass it is possible to obtain in just 30 minutes a cellulosic pulp at about 50% weight yield. The spent SEW liquor containing most of the hemicelluloses and lignin after pulp washing is then conditioned in a 4-step "conditioning" process producing a fermentable aqueous sugar stream of close to 100 g/L and precipitated lignosulfonate. The key aspects of the invention are:

1. The high $SO_2$ concentration at 150° C. during fractionation which leads to a very short fractionation time (30 minutes), and minimizes "condensation" of the lignosulfonate to a "char-like" material during "conditioning" of the spent SEW liquor.
2. The 4-step conditioning process after fractionation at high $SO_2$ concentration which minimizes sugar degradation during "conditioning" to only 10% (of the originally dissolved hemicelluloses) while removing 99.8% of $SO_2$ and recovering most of the ethanol.
3. The 4-step conditioning process which reduces the final dissolved $SO_2$ concentration in the aqueous sugar stream to 10 ppm or below and also removes potential inhibitors from the solution so that it is fermentable to butanol by Clostridia bacteria.

The procedure described in the present invention for SEW fractionation of wood material, preferably wood chips, e.g. spruce chips, and subsequent spent liquor conditioning for final ABE fermentation produces a conditioned liquor of high monomeric and total sugar concentrations. It was surprisingly found that it is possible still to reduce the sugar losses detected earlier. Consequently, in the process of the present invention the total sugar mass balance loss for the entire conditioning process is as low as 10% with most of the losses occurring during vacuum evaporation which increases the effective acidic conditions at relatively high temperature. The sugar losses during rotovap evaporation amount to approximately 6%. Ethanol and unreacted $SO_2$ are fully removed from the conditioned liquor and will be recycled in an industrial application. Fermentation inhibitors such as furfural, HMF, acetic acid, formic acid and aldonic acids are present in negligible quantities in the final conditioned liquor.

It was also surprisingly found that it is possible to totally remove the fermentation inhibitors, such as $SO_2$, ethanol, lignin, formic acid and furanic compounds, from the solution so that it is fermentable to butanol by Clostridia bacteria. This goal is achieved by carrying out a final catalytic oxidation step in order to convert residual sulfite ions to sulfate ions by oxidation. This final step is carried out by adding oxidation catalyst ($FeSO_4.7H_2O$) that oxidizes sulfite ions to sulfate. It is notable that an additional function of the oxidation catalyst is that it serves as a micronutrient source for Clostridia bacteria. While this is a well-known practice, i.e. $FeSO_4.7H_2O$ is a common medium component for ABE fermentation (Junelles et al. 1988), in the present invention this micronutrient may be directly carried forward from the final conditioning step with the conditioned liquor to the fermentation.

The final 10-fold reduction of $SO_2$ to 10 ppm by the liming and catalytic oxidation is important since the Clostridia bacteria have a low tolerance to $SO_2$ (intoxication effect). Furthermore, by reaching 10 ppm $SO_2$ concentration in the conditioned liquor it is ensured that the Clostridia bacteria can produce butanol, acetone and ethanol without any $SO_2$ intoxication taking place. Previous research by the present inventors has shown that liming itself (not followed by catalytic oxidation) is not enough to stimulate chemicals production by the Clostridia bacteria. The Clostridia bacteria do survive after liming to pH 9 but chemicals production is problematic. We therefore consider catalytic oxidation step as an essential part of the conditioning process of the present invention.

The Clostridium family includes a few genera which can be used in ABE fermentation. Advantageous bacteria useful in the present invention are of the species *Clostridium acetobutylicum*.

The present invention is unique and compelling because it can utilize cheap raw materials such as lignocellulosic forestry residues to produce value added chemicals i.e. butanol for use as transport fuel. These raw materials do not compete with food production as is the case with ethanol/butanol production from starch. A key advantage of the invention is that it can be retrofitted to existing pulp and paper mills to improve their revenue. Also the sugar yield from the hemicelluloses is very high (about 90%), no external acid is needed for the hydrolysis of the dissolved hemicelluloses, the fractionation process takes only 30 minutes, and it is omnivorous i.e. applies to hardwoods, softwoods and annual plant fibers.

The process described in the present specification can be applied also to other raw materials besides wood chips, i.e. all kind of mixed forest biomass and mixed softwood biomass, even empty fruit bunches etc. Preliminary results from fermentation trials show that all conditioned liquors are fermentable to acetone/isopropanol, ethanol, butanol by Clostridia bacteria. All of these experiments have been performed at a laboratory scale so far, using spruce chips as raw material. The next stage of development work will involve scaling up SEW fractionation and "conditioning" process to pilot scale volumes (100-400 L) so that more realistic process conditions are investigated.

Experimental

SEW Pulping

Spruce chips were air dried and screened using 4 mm and 2 mm hole screens. SEW fractionation was done in a HAATO 43427 silicon oil bath using simultaneously six 220 mL bombs with 25 g oven dry (O.D.) spruce chips in each bomb. Moisture content of the chips was taken into consideration to allow for the correct weight of spruce chips inside each bomb. The fresh liquor was prepared by bubbling $SO_2$ (scientific grade $SO_2$ 3.8 from Linde AG, Germany, purity of 99.98%) through the 55% (by volume) ethanol-water solution cooled in an ice bath at a low flow rate for approximately 30 minutes to dissolve the set amount of 12% by weight as measured continuously using an electronic balance. Ethanol used was ETAX (purity of 96.1% vol.). The liquor-to-wood ratio used for pulping was 3 L kg$^{-1}$. The temperature of the oil bath was set to 150° C. (±1° C.) and pulping time was 30 minutes. After fractionation, the bombs were rapidly removed from the oil bath and cooled in cold water. SEW spent liquor (about 300 ml) was collected by squeezing the pulp suspension contained in a washing sock. A hydraulic press was used for this purpose. The pulp was then washed twice with 210 mL of 40% ethanol-water at 60° C. and three times with 210 mL of deionized water at room temperature. The washings were added to the SEW liquor. The liquor so obtained was designated as MSEW liquor.

Conditioning Steps

Figure 3:
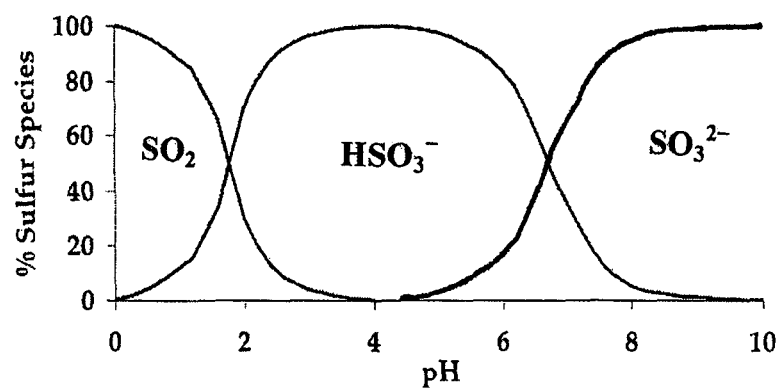

The MSEW liquor was exposed to a sequence of "conditioning" steps as presented in FIG. 1. As the first conditioning step, the MSEW liquor was treated in a rotary evaporator for 120 minutes to remove $SO_2$ and ethanol. The water bath temperature was 95° C. and the vacuum 200 mbar. These conditions were chosen to obtain a reasonable evaporation rate and time to reduce the ethanol concentration in the liquor to approx. 1.1 g L$^{-1}$ (determined using an ethanol assay kit from Megazyme International, Ireland). About 71.8% of the original weight was evaporated to reach this goal. The rotovap treated liquor called EVAP did not contain any char-like material. Consequently, no lignin condensation took place. The EVAP liquor was centrifuged, whereby a light-coloured precipitate was obtained. Steam stripping was carried out for 120 minutes in order to further remove $SO_2$ to a level of approximately 100 ppm. In the liming step the steam-stripped liquor called STR was neutralized by addition of $Ca(OH)_2$ to pH 8.9 to obtain LIME liquor. Liming to pH 8.9 led also to precipitation of $SO_2$ (present predominantly in the form of sulfite ions, FIG. 3) in the form of calcium lignosulfonate precipitate. This precipitate was removed by centrifugation (11000 rpm for 15 min) and washed three times with alkaline water. The wash waters collected as supernatants after the centrifugations were added to the neutralized LIME liquor. Finally, the remaining sulphite anions in the liquor were catalytically oxidized to sulphate by addition of $FeSO_4.7H_2O$ as catalyst at about 20 mg $L^{-1}$ and bubbling air through the solution at 60° C. for 1 hour with air flow rate of <0.2 L/min. The conditioned liquor called CATOX was then used for fermentation utilizing Clostridia bacteria.

Pulp and Liquor Analyses

The pulp and dissolved components yield in all the liquors was determined by evaporation to dryness at 105° C. (SCAN-C3:78 and SCAN-N1:61, respectively). Ash content of the pulp and dried liquor samples was analyzed according to NREL/TP-510-42622. Extractives were removed from the pulp with acetone and analyzed gravimetrically (SCAN 49:03) while the spent liquor samples were evaporated to dryness in a Rotavap, prior to the determination of total carbohydrates, lignin and (in pulp) acetyl groups within the same procedure (NREL/TP-510-42618). The analysis comprised of a two stage sulfuric acid hydrolysis. The first stage was performed at 72% $H_2SO_4$, acid-to-material ratio of about 2-5 mL $g^{-1}$ (for the liquors) and about 10 mL $g^{-1}$ (for the pulp), 30±3° C. and 60±5 min, while the second stage at 4% $H_2SO_4$, acid-to-material ratio of 50-130 mL $g^{-1}$ (for the liquors) and 300 mL $g^{-1}$ (for the pulp), 121±1° C. and 60 min. The resulting monosaccharides and acetic acid were measured by HPAEC (Dionex ICS-3000, CarboPac PA20 column, Pulsed amperometric detection (PAD)) and HPLC (Dionex UltiMate 3000, Acclaim OA column, Diode array detector), respectively. Acid insoluble lignin was determined gravimetrically whereas acid soluble lignin was determined by measuring absorbance at 205 nm using a Shimadzu UV-2550 spectrophotometer. An extinction coefficient of 128 L $g^{-1}$ $cm^{-1}$ was used (Iakovlev and van Heiningen, 2011).

The pulp was also analyzed for kappa number (SCAN-C 1:00).

Mono sugar concentrations in the process liquors after each conditioning step were analyzed by HPAEC-PAD (Dionex ICS 3000, Sunnyvale, Calif., USA) according to NREL/TP-510-42623. Furfural and hydroxymethylfurfural in all process liquors were analyzed using a Dionex UltiMate 3000 HPLC with diode array detector. Acetic acid and formic acid in all process liquors were analyzed using a HP 1100 HPLC. Aldonic acids in all process liquors were analyzed by HPAEC equipped with a Dionex CarboPac PA10 4*250 mm column and ED50 Pulse Amperometric Detector. Uronic acids in pulp and in all process liquors were analyzed by methanolysis/GC-FID using a Shimadzu GC-17A gas chromatograph with NB-30 capillary column (length 30 m, internal diameter 0.32 mm) according to Sundberg et al. 1996. All process liquors were analyzed to determine their sulfate and sulfite anions (after adding NaOH) concentration by ion chromatography (Dionex ICS 1500, Sunnyvale, Calif., USA). Finally, sulphur content in the precipitate was measured by combustion with oxygen in a Schöniger flask, followed by absorption of sulphur dioxide in hydrogen peroxide solution. The formed sulfate anions were determined by the ion chromatography (SCAN-CM 57:99).

Results

Lignin Analysis

Lignin concentrations for each process liquor produced during conditioning are presented in Table 1. Lignin mass balances on the original wood, the pulp and the process liquors are presented in Table 2. The lignin concentration in SEW spent liquor is 59.8 g $L^{-1}$ and the corresponding total amount of lignin is 11.6 g/100 g O.D. wood. Addition of the pulp washings produces MSEW liquor having a lignin concentration of 21.6 g $L^{-1}$ and a corresponding total amount of lignin of 17.8 g/100 g O.D. wood. Lignin concentration in EVAP liquor is 22.0 g $L^{-1}$ and the corresponding total amount of lignin is 4.1 g/100 g O.D. wood. This major reduction in the total amount of lignin is associated with the precipitate formed during rotovap evaporation. A simple mass balance calculation shows that a major part of the difference in the amount of total lignin before and after evaporation is due to the amount of precipitate that is formed during rotovap evaporation. The amount of precipitate formed is equal to 10.3 g/100 g O.D. wood whereas the total lignin difference before and after evaporation is equal to 13.7 g/100 g O.D. wood. According to sulphur analysis results the precipitate contains 1.1% wt. sulphur. It is known from acid sulfite pulping that lignin condensation favoured by high acidity and high temperature may be reduced by increasing the concentration of free $SO_2$ (i.e. the Kaufmann diagram shown by Rydholm 1965). The evaporation of ethanol increases the effective acidity of the EVAP liquor at 95° C. However, the high free $SO_2$ concentration prevents lignin condensation reactions from happening. It is therefore likely that the precipitate is uncondensed lignin. Further evidence that the precipitate is uncondensed lignin is the fact that a dramatic decrease in acid-insoluble lignin values for EVAP liquor compared to MSEW is observed when the precipitate is formed. The lignin concentration in STR, LIME and CATOX liquors is progressively reduced, with the lignin amount on wood of 3.7, 3.7 and 3.0 g/100 g O.D. wood respectively. Lignin in CATOX liquor is for 90% in acid soluble form.

Total Sugars

Total sugar concentration, i.e. the sum of the monomers and oligomers (calculated as monomers) for each of the five hemicellulose neutral sugars are also presented in Table 1. It can be seen that the total sugar concentration in SEW spent liquor is 56.8 g $L^{-1}$. The total sugar concentration in the MSEW liquor decreases to 23.2 g $L^{-1}$ due to the approximately 4-fold dilution with the pulp washings. The total sugar concentration in the EVAP liquor increases to 95.9 g $L^{-1}$ due to the volume reduction of a factor 4.4 after evaporation of more than 99% of the ethanol and removal of about 90% of the $SO_2$ from the SEW liquor. Some water is also removed. After steam stripping the total sugar concentration in STR liquor drops slightly to 95.1 g $L^{-1}$. Subsequent liming by addition of $Ca(OH)_2$ further reduces total sugars concentration due to dilution with water from the precipitate washings which are added to the neutralized mother liquor. The total sugar concentration in the LIME liquor is 88.2 g $L^{-1}$. After the final catalytic oxidation step where 3.3 mg of catalyst ($FeSO_4.7H_2O$) are added to 155 mL LIME liquor, the total sugars concentration in final CATOX liquor increases to 94.8 g $L^{-1}$ due to some water evaporation. In all liquors the predominant sugar is mannose derived from the main hemicellulose of spruce, galactoglucomannan.

Total Sugar Mass Balance (as Anhydrosugars)

The anhydrosugar mass balance on wood for each stage of the conditioning process is presented in Table 2. The total amount of anhydrosugars based on the original amount of wood in the SEW spent liquor is 9.9 g/100 g O.D. wood. Addition of the pulp washings results in 17.1 g/100 g O.D. wood anhydrosugars in MSEW liquor corresponding to approximately ⅓ of the sugars present in the spruce chips. There are minor sugar losses of only 5% after cooking at conditions of 12% wt. $SO_2$, 150° C., 30 minutes and washing of the pulp. The difference between the carbohydrate content in the original wood and pulp is 20.9 g/100 g wood (see Table 2), which is fairly close to the anhydrosugars content of the MSEW liquor of 17.1 g/100 g O.D. wood. The amount of anhydrosugars in the EVAP liquor is reduced to 16.0 g/100 g O.D. wood. This result suggests that there are modest sugar losses of only 6% relative to MSEW liquor during rotovap evaporation. A possible explanation for this is that during evaporation of ethanol at 95° C. the effective acidity of the liquor increases (pH of about 0.8) resulting in sugar degradation. The major sugar degradation products are furfural (pentose degradation) and hydroxymethylfurfural (hexose degradation). Other degradation products include acetic, formic and aldonic acids. However, their contribution to sugar losses is very small. Concentrations and amounts on O.D. wood basis for the latter are presented in Tables 1 and 2. Total amount of anhydrosugars in STR liquor is 15.8 g/100 g O.D. wood which equals approximately to 7.5% of sugar losses relative to MSEW liquor. The additional 1.5% sugar losses are probably again due to acid degradation during treatment with steam. The remaining liquor conditioning steps of LIME and CATOX do not seem to cause significant additional sugar losses; with total amount of anhydrosugars of 15.4 g/100 g O.D. wood for both liquors. Thus the largest total sugar mass balance loss occurs during rotovap evaporation and all the other liquor conditioning steps have a minor effect on sugar losses.

Monomeric and Oligomeric Sugars

The amounts of monomeric and oligomeric sugars in each liquor produced during the conditioning process are presented in Table 1. The percentage of oligomers in the SEW liquor is 37.0% on average. Addition of the pulp washings increases percentage of oligomers in MSEW liquor to 49.0% on average. The strong acidic conditions during rotovap evaporation reduce the percentage of oligomers to 37.1% on average in the EVAP liquor. Steam stripping for two hours further reduces the percentage of oligomers in STR liquor to 31.3% on average. Liming by addition of $Ca(OH)_2$ further reduces the average percentage of oligomers to 20.3%, while the percentage of oligomers in CATOX liquor is only 19.6%, with arabinose existing by approximately 90% in monomeric form. The analysis of oligomers for CATOX liquor also shows that glucomannan is most resistant to hydrolysis with percentages of mannan and glucan of 27.6% and 33.5%, respectively. This is in agreement with the lower acid hydrolysis rate of methyl-mannopyranosides and glucopyranosides compared to methyl-xylopyranosides and galactopyranosides (Feather and Harris, 1965).

Overall it is shown that in the course of the conditioning the monomeric sugar concentration is doubled, i.e. from 35.3 g $L^{-1}$ in SEW spent liquor to 72.6 g $L^{-1}$ in the final CATOX liquor. This increase is beneficial for the fermentation and economy of the biofuels production process.

Furfural and Hydroxymethylfurfural

The furfural and hydroxymethylfurfural (HMF) analysis results for each liquor are presented in Tables 1 and 2. The results show that the furfural and HMF concentrations in SEW liquor are 0.5 and 0.2 g $L^{-1}$, respectively or 0.1 g/100 g O.D. wood and zero levels calculated as their respective pentose and hexose precursors. This shows that sugar dehydration during SEW fractionation is minimal. Addition of the pulp washings slightly increases furfural and HMF amounts to 0.2 and 0.1 g/100 g O.D. wood, respectively. After rotovap evaporation and despite the associated volume reduction by a factor of 4.4, the furfural concentration in the EVAP liquor is reduced to zero levels because of evaporation as an azeotrope with water (35% furfural in water at 97.85° C.; Zeitsch, 2000). The HMF concentration on the other hand increases to 0.5 g $L^{-1}$ in EVAP liquor because HMF is not volatile by steam (Sjöström, 1993). Also more HMF may be formed during the EVAP from the C6 sugars, but then be partly further converted to levulinic acid and formic acid and unidentified condensation products called "humins" (Girisuta et al., 2006) The latter are formed at a fractional yield of 35% or more of the conversion of C6 sugars or HMF, and are quantified as an insoluble black precipitate (Girisuta et al., 2006). Thus part of the earlier identified sugar loss occurring during the rotovap operation may be due to formation and evaporation of furfural and formation and degradation of HMF. Evidence of the latter is the formation of formic acid during EVAP as will be discussed below. Furfural was non-detectable in the STR, LIME and CATOX liquors confirming that furfural is rapidly removed during steam stripping. The HMF concentration in STR, LIME and CATOX liquors is gradually reduced to 0.3 g $L^{-1}$ in CATOX liquor. Tests in our laboratory (Teräsvuori et al., 2010) showed that Clostridia are not affected by HMF up to a concentration of 1.5 g/L.

Other Potential Fermentation Inhibitors

The results for acetic acid and formic acid are presented in Tables 1 and 2. The acetic acid concentration is 2.4 g $L^{-1}$ (0.5 g/100 g O.D. wood) and the formic acid concentration is close to zero in SEW liquor. Addition of the pulp washings results in acetic and formic acid concentrations of 1.3 g $L^{-1}$ and 0.1 g $L^{-1}$, respectively in MSEW liquor. After rotovap evaporation and due to the associated volume reduction the acetic acid concentration in the EVAP liquor is increased to 2.1 g $L^{-1}$. However, based on original wood this is only 0.4% showing that the majority of acetic acid is evaporated. The formic acid concentration slightly increases to 0.2 g $L^{-1}$ after rotovap treatment, most likely due to HMF degradation in the strongly acidic EVAP solution. Evaporation of formic acid and acetic acid takes place during the subsequent steam stripping operation so that their concentrations are reduced to negligible levels in the STR liquor and subsequent process liquors. It was found (Teräsvuori et al., 2010) that acetic acid does not inhibit the fermentation by Clostridia.

Total Mass Balance

The total mass balance based on comparison of the identified components in the original wood, pulp and conditioning liquors is shown in Table 2. The sum of the identified components in the pulp and MSEW liquor is 85.6% which is quite close to the 97.0% total for the original wood considering the intensive pulp washing steps that took place. The sum of the mass of the components in the EVAP liquor, pulp and precipitate decreases to 82.5% mainly due to the earlier noted sugar losses. At the end of the conditioning process the total solids identified account for 81.4% of the original wood weight.

Inorganic Sulfur Species

The sulfite and sulfate anions results of each process liquor produced during conditioning are presented in Table 3. It shows that the $SO_2$ concentration in the fresh cooking liquor is 63.5 g $L^{-1}$ representing a charge of 35.2 g/100 g O.D. wood. The amount of $SO_2$ consumed during SEW cooking based on the residual $SO_2$ concentration in SEW spent liquor of 34.2 g $L^{-1}$ (or 6.6 g/100 g O.D. wood) is 28.6 g/100 g O.D. wood. The concentration of $SO_2$ is progressively reduced to 8.1 g $L^{-1}$ in the MSEW liquor, then to 4.9 g $L^{-1}$ in the EVAP liquor, then to 101 ppm in the STR liquor and finally 10 ppm in the CATOX liquor. The sulfate anions concentration increased from about 0.9 g $L^{-1}$ in MSEW liquor to 2.7 g $L^{-1}$ in EVAP liquor due to the volume reduction during this conditioning step. Sulfate concentration remained at the same levels in STR liquor, i.e. at 2.8 g $L^{-1}$. After the catalytic oxidation step sulfate concentration increased from 3.1 g $L^{-1}$ in LIME liquor to 3.8 g $L^{-1}$ in CATOX liquor. The latter is due to addition of the oxidation catalyst ($FeSO_4.7H_2O$) that oxidized sulfite ions to sulfate. An additional function of the oxidation catalyst is that it serves as a micronutrient source for Clostridia bacteria.

The $SO_2$ mass balance calculations based on Table 3 show that approximately 90% wt. of $SO_2$ is removed by rotovap evaporation and that nearly all remaining $SO_2$ is removed by steam stripping. The use of extra pure $SO_2$ during SEW cooking ensures that our mass balance calculations are as accurate as possible. As indicated above, the final 10-fold reduction of 101 ppm $SO_2$ to 10 ppm by the liming and catalytic oxidation is important since the Clostridia bacteria have a low tolerance to $SO_2$. Consequently, by reaching 10 ppm $SO_2$ concentration in CATOX liquor we ensured that the Clostridia bacteria can produce butanol, acetone and ethanol without any $SO_2$ intoxication taking place.

ABE Fermentation

Preliminary results from batch fermentation tests with Clostridia bacteria are promising. Different dilutions of the final conditioned liquor (CATOX) with cells and MSS growth media show moderate to strong cell growth. Moreover, the observed sporulation of the bacteria cells indicates production of chemicals. Measurements by HPLC showed that solvents are produced a total concentration of approximately 9 g $L^{-1}$. Butanol is produced at a concentration of 5.2 g $L^{-1}$, acetone is produced at a concentration of 2.8 g $L^{-1}$, and ethanol is produced at a concentration of 0.8 g $L^{-1}$. Fermentation studies show that it is possible to produce up to 4.0 g $L^{-1}$ isopropanol instead of acetone by using different *Clostridium* bacteria or by using genetically modified *E. coli* strain (Jurgens et al., 2010) to ferment the conditioned liquor.

TABLE 1

Sugar and other organic compounds concentrations

| Liquor | SEW | MSEW | EVAP | STR | LIME | CATOX |
|---|---|---|---|---|---|---|
| pH | 1.0 | 1.1 | 0.8 | 1.1 | 8.9 | 7.2 |
| Monomeric sugars (g $L^{-1}$) | | | | | | |
| Carbohydrates | 35.3 | 11.9 | 59.2 | 63.2 | 66.8 | 72.6 |
| Arabinose | 1.9 | 0.7 | 3.8 | 4.0 | 4.2 | 4.6 |
| Xylose | 8.3 | 2.8 | 13.9 | 15.3 | 16.5 | 18.0 |
| Mannose | 16.1 | 5.5 | 26.3 | 28.2 | 30.0 | 32.8 |
| Galactose | 3.4 | 1.1 | 6.4 | 6.9 | 7.1 | 7.8 |
| Glucose | 5.5 | 1.9 | 8.9 | 8.9 | 9.1 | 9.5 |
| Total sugars (as monomers) (g $L^{-1}$) | | | | | | |
| Carbohydrates | 56.8 | 23.2 | 95.9 | 95.1 | 88.2 | 94.8 |
| Arabinose | 2.9 | 1.2 | 5.1 | 5.1 | 4.7 | 5.0 |
| Xylose | 12.6 | 5.1 | 21.7 | 21.4 | 19.9 | 21.4 |
| Mannose | 27.0 | 11.0 | 45.4 | 45.1 | 41.8 | 44.9 |
| Galactose | 5.5 | 2.3 | 8.8 | 9.0 | 8.3 | 8.9 |
| Glucose | 8.7 | 3.7 | 14.9 | 14.7 | 13.5 | 14.6 |
| % oligomers | | | | | | |

TABLE 1-continued

Sugar and other organic compounds concentrations

| Liquor | SEW | MSEW | EVAP | STR | LIME | CATOX |
|---|---|---|---|---|---|---|
| Carbohydrates | 37.0 | 49.0 | 37.1 | 31.3 | 20.3 | 19.6 |
| Arabinose | 34.1 | 43.5 | 24.0 | 20.2 | 10.7 | 9.0 |
| Xylose | 34.0 | 45.9 | 34.5 | 27.3 | 16.9 | 15.6 |
| Mannose | 41.8 | 51.1 | 41.3 | 37.3 | 28.8 | 27.6 |
| Galactose | 38.5 | 49.8 | 26.2 | 22.5 | 13.4 | 12.5 |
| Glucose | 36.6 | 48.5 | 38.5 | 38.1 | 31.6 | 33.5 |
| Other organic compounds (g $L^{-1}$) | | | | | | |
| Lignin | 59.8 | 21.6 | 22.0 | 19.7 | 19.6 | 16.5 |
| Acid insoluble | 52.1 | 19.2 | 6.8 | 4.6 | 4.5 | 1.4 |
| Acid soluble | 7.7 | 2.4 | 15.2 | 15.1 | 15.1 | 15.1 |
| Furfural | 0.5 | 0.2 | 0.0 | n.d | n.d | n.d |
| HMF | 0.2 | 0.1 | 0.5 | 0.5 | 0.3 | 0.3 |
| Acetic acid | 2.4 | 1.3 | 2.1 | 0.2 | 0.2 | 0.3 |
| Formic acid | 0.2 | 0.1 | 0.2 | 0.1 | 0.0 | 0.0 |
| Xylonic acid | n.d | n.d | n.d | n.d | n.d | n.d |
| Mannonic acid | 0.0 | n.d | 0.0 | 0.0 | 0.0 | 0.0 |
| Glucuronic acid | 1.3 | 0.4 | 5.0 | 4.4 | 3.7 | 3.9 |
| Galacturonic acid | 2.2 | 0.7 | 10.1 | 8.2 | 6.8 | 7.2 |
| 4-O—Me-glucuronic acid | 0.5 | 0.2 | 3.1 | 2.8 | 2.3 | 2.4 | n.d = not detected

TABLE 2

Mass balance on original wood, pulp and conditioning liquors

| Solid phase composition (% on wood) | spruce chips | pulp |
|---|---|---|
| Carbohydrates | 62.2 | 41.3 |
| Arabinan | 1.1 | 0.0 |
| Xylan | 5.6 | 1.2 |
| Mannan | 10.8 | 1.6 |
| Galactan | 2.5 | 0.0 |
| Glucan | 42.2 | 38.5 |
| Extractives | 1.5 | 1.3 |
| Lignin | 28.9 | 5.0 |
| Acid insoluble | 28.3 | 4.7 |
| Acid soluble | 0.6 | 0.3 |
| Ash | 0.3 | 0.0 |
| Acetyl groups | 1.1 | 0.0 |
| Uronic acids | 3.0 | 0.2 |
| Total in solid phase | 97.0 | 47.8 |

| Liquors composition (% on wood) | SEW | MSEW | EVAP | STR | LIME | CATOX |
|---|---|---|---|---|---|---|
| Carbohydrates | 9.9 | 17.1 | 16.0 | 15.8 | 15.4 | 15.4 |
| Arabinose | 0.5 | 0.8 | 0.8 | 0.8 | 0.8 | 0.8 |
| Xylose | 2.2 | 3.7 | 3.6 | 3.5 | 3.4 | 3.4 |
| Mannose | 4.7 | 8.2 | 7.6 | 7.5 | 7.3 | 7.3 |
| Galactose | 1.0 | 1.7 | 1.5 | 1.5 | 1.5 | 1.5 |
| Glucose | 1.5 | 2.7 | 2.5 | 2.5 | 2.4 | 2.4 |
| Lignin | 11.6 | 17.8 | 4.1 | 3.7 | 3.7 | 3.0 |
| Acid insoluble | 10.1 | 15.8 | 1.3 | 0.9 | 0.9 | 0.3 |
| Acid soluble | 1.5 | 2.0 | 2.8 | 2.8 | 2.9 | 2.7 |
| Precipitated lignin* | | | 10.3 | 10.3 | 10.3 | 10.3 |
| Furfural | 0.1 | 0.2 | 0.0 | n.d | n.d | n.d |
| HMF | 0.0 | 0.1 | 0.1 | 0.1 | 0.1 | 0.1 |
| Ash | 0.2 | 0.5 | 0.4 | 0.4 | 3.4 | 2.4 |
| Acetic acid | 0.5 | 1.0 | 0.4 | 0.0 | 0.0 | 0.0 |
| Formic acid | 0.0 | 0.0 | 0.0 | 0.0 | 0.0 | 0.0 |
| Xylonic acid | n.d | n.d | n.d | n.d | n.d | n.d |
| Mannonic acid | 0.0 | n.d | 0.0 | 0.0 | 0.0 | 0.0 |
| Glucuronic acid | 0.3 | 0.3 | 0.9 | 0.8 | 0.7 | 0.7 |
| Galacturonic acid | 0.4 | 0.6 | 1.9 | 1.5 | 1.3 | 1.3 |
| 4-O—Me- | 0.1 | 0.2 | 0.6 | 0.5 | 0.4 | 0.4 |

TABLE 2-continued

Mass balance on original wood, pulp and conditioning liquors

| glucuronic acid | | | | | | |
|---|---|---|---|---|---|---|
| Total in liquor | 23.1 | 37.8 | 34.7 | 33.1 | 35.4 | 33.6 |
| Total in solid phase and liquor (% on wood) | 70.9 | 85.6 | 82.5 | 80.9 | 83.2 | 81.4 |

*Precipitated lignin was removed from the liquor after rotovap evaporation and its amount is included in the mass balance for EVAP, STR, LIME and CATOX liquors
n.d = not detected

TABLE 3

Ion Chromatography analysis results

| | cooking liquor | SEW | MSEW | EVAP | STR | LIME | CATOX |
|---|---|---|---|---|---|---|---|
| Concentration (mg L$^{-1}$) | | | | | | | |
| $SO_3^{2-}$ | | 42777 | 10062 | 6078 | 126 | 25 | 12 |
| $SO_4^{2-}$ | | 2673 | 881 | 2690 | 2783 | 3064 | 3797 |
| $SO_2$/equivalent $SO_2$ | 63482 | 34222 | 8050 | 4862 | 101 | 20 | 10 |
| $SO_2$ on wood (%) | 35.2 | 6.6 | 6.6 | 0.9 | 0.2 | 0.0 | 0.0 |

REFERENCES

Dürre, P. (2008) Fermentative butanol production: bulk chemical and biofuel. Ann. N.Y. Acad. Sci. 1125, 353-362.

Feather, M. S., Harris, J. F. (1965) The acid-catalyzed hydrolysis of glycopyranosides. J. Org. Chem. 30 (1):153-157.

Girisuta, B., Janssen, L. P. B. M., Heeres, H. J. (2006) A kinetic study on the decomposition of 5-hydroxymethyl-furfural into levulinic acid. Green Chemistry 8 (8): 701-709.

Iakovlev, M., van Heiningen, A. (2011) $SO_2$ ethanol-water (SEW) pulping: I. Lignin determination in pulps and liquors. Journal of wood chemistry and technology. 31 (3): 233-249.

Iakovlev, M., Sixta, H., van Heiningen, A. (2011) $SO_2$ ethanol-water (SEW) pulping: II. Kinetics for spruce, beech and wheat straw. Journal of wood chemistry and technology. 31 (3): 250-266.

Jurgens, G., Granstrom, T. B., van Heiningen, A. (2010) Cloning and expression of primary-secondary alcohol dehydrogenase gene from *Clostridium Beijerinckii* as a part of the project of producing biofuels from forest biomass. Poster at *Clostridium* 11 conference, October 3-6, San Diego, USA.

Junelles, A. M., Janati-Idrissi, R., Petitdemange, H., Gay, R. (1988) Iron Effect on Acetone-Butanol Fermentation. Current Microbiology. 17: 299-303.

Rakkolainen, M., Pylkkanen, V., van Heiningen, A. (2009) Commodity Chemicals from Forest Biomass, Proceedings 7$^{th}$ Biennial Johan Gullichsen Colloquium—FOREST BIOMASS—QUO VADIS? Nov. 19, 2009, Espoo, Finland, 57-63

Rakkolainen, M., Iakovlev, M., Teräsvuori, A.-L., Sklavounos, E., Jurgens, G., Granström, T. B., van Heiningen, A. (2010) $SO_2$-ethanol-water fractionation of forest biomass and implications for biofuel production by ABE fermentation. Cellulose Chemistry and Technology, 44 (4-6):139-145.

Retsina, T., Pylkkänen, V. (2007) Back to the biorefinery: a novel approach to boost pulp mill profits. *Paper 360°*, February issue, 18-19.

Rydholm, S. A. (1965) Pulping Processes, John Wiley and Sons, Inc., 467

Sjöström, E. (1993) Wood chemistry: fundamentals and applications. Academic Press, 231

Sklavounos, E., van Heiningen, A. (2010) $SO_2$-ethanol-water fractionation of spruce and spent liquor conditioning for ABE fermentation. In: The 11th European workshop on lignocellulosics and pulp (EWLP, Proceedings). Hamburg, Germany, 16-19 August, pp. 205-208.

Sundberg, A., Sundberg, K., Lillandt, C., Holmbom, B. (1996) Determination of hemicelluloses and pectins in wood and pulp fibers by acid methanolysis and gas chromatography. Nordic Pulp & Paper Research Journal, 11 (4):216-219.

Teräsvuori, A-L., Jurgens, G. and Granström T. (2010), Unpublished results, Aalto University, Espoo, Finland.

Zeitsch, K. J. (2000) The chemistry and technology of furfural and its many by-products, Elsevier, Amsterdam, 75.

The invention claimed is:

1. A method for conditioning of a biomass-derived liquor containing sulfur dioxide, said method comprising:
    (a) obtaining a first liquor derived from cooking and washing a biomass feedstock, wherein said first liquor comprises sulfur dioxide, water, hemicelluloses, and lignin;
    (b) evaporating and stripping said first liquor to remove a first amount of sulfur dioxide, thereby generating a second liquor;
    (c) increasing the pH of said second liquor to precipitate and remove a second amount of sulfur dioxide, in the form of lignosulfonate, thereby generating a third liquor comprising sulfite anions; and
    (d) exposing said third liquor to catalytic oxidation in the presence of a ferrous sulfate-based catalyst and an oxidant under effective reaction conditions to oxidize said sulfite anions to sulfate anions, thereby generating a conditioned liquor.

2. The method of claim 1, wherein said biomass is selected from hardwoods, softwoods, annual plant fibers, or combinations thereof.

3. The method of claim 1, wherein said first liquor further comprises ethanol.

4. The method of claim 1, wherein said stripping in step (b) is steam stripping.

5. The method of claim 1, said method further comprising separating a lignin-containing precipitate during step (b).

6. The method of claim 1, wherein said pH of said second liquor is at least 7.

7. The method of claim 1, wherein during step (c), said pH of said second liquor is increased by addition of lime, and wherein said lignosulfonate is calcium lignosulfonate that precipitates from said second liquor.

8. The method of claim 1, wherein said ferrous sulfate-based catalyst is ferrous sulfate heptahydrate, $FeSO_4 \cdot 7H_2O$.

9. The method of claim 1, said method further comprising fermenting said conditioned liquor with Clostridia bacteria.

10. The method of claim 9, wherein said Clostridia bacteria are of species *Clostridium acetobutylicum*.

11. A process for fractionating biomass to prepare sugars for bacterial fermentation, said process comprising:
   (a) exposing a biomass feedstock to a liquid solution comprising sulfur dioxide, water, and an aliphatic alcohol, under effective cooking conditions to generate pulp;
   (b) pressing and washing said pulp to separate washed pulp from spent liquor, and recover each of said spent liquor and said washed pulp, wherein said spent liquor comprises sulfur dioxide, water, aliphatic alcohol, hemicelluloses, and lignin;
   (c) evaporating and stripping said spent liquor to remove a first amount of sulfur dioxide, thereby generating a stripped liquor;
   (d) increasing the pH of said stripped liquor to precipitate and remove a second amount of sulfur dioxide, in the form of lignosulfonate, thereby generating a pH-adjusted liquor comprising sulfite anions; and
   (e) exposing said pH-adjusted liquor to catalytic oxidation in the presence of a ferrous sulfate-based catalyst and an oxidant under effective reaction conditions to oxidize said sulfite anions to sulfate anions, thereby generating a conditioned liquor containing sugars suitable for bacterial fermentation.

12. The process of claim 11, wherein said biomass is selected from hardwoods, softwoods, annual plant fibers, or combinations thereof.

13. The process of claim 11, wherein said aliphatic alcohol is ethanol.

14. The process of claim 11, wherein said stripping in step (c) is steam stripping.

15. The process of claim 11, said process further comprising separating a lignin-containing precipitate during step (c).

16. The process of claim 11, wherein said pH of said pH-adjusted liquor is at least 7.

17. The process of claim 11, wherein during step (d), said pH of said pH-adjusted liquor is increased by addition of lime, and wherein said lignosulfonate is calcium lignosulfonate that precipitates from said pH-adjusted liquor.

18. The process of claim 11, wherein said ferrous sulfate-based catalyst is ferrous sulfate heptahydrate, $FeSO_4 \cdot 7H_2O$.

19. The process of claim 11, said process further comprising fermenting said conditioned liquor with Clostridia bacteria.

20. The process of claim 19, wherein said Clostridia bacteria are of species *Clostridium acetobutylicum*.

* * * * *